(12) United States Patent
Tebbi

(10) Patent No.: US 12,091,717 B1
(45) Date of Patent: Sep. 17, 2024

(54) SYSTEM AND METHOD FOR THE DETECTION AND PREVENTION OF LEUKEMIA AND LYMPHOMA

(71) Applicant: Cameron Kamran Tebbi, Tampa, FL (US)

(72) Inventor: Cameron Kamran Tebbi, Tampa, FL (US)

(*) Notice: Subject to any disclaimer, the term of this patent is extended or adjusted under 35 U.S.C. 154(b) by 0 days.

(21) Appl. No.: 18/129,791

(22) Filed: Mar. 31, 2023

(51) Int. Cl.
 C12Q 1/6886 (2018.01)
 A61K 39/00 (2006.01)

(52) U.S. Cl.
 CPC ........ *C12Q 1/6886* (2013.01); *A61K 39/0002* (2013.01); *A61K 2039/585* (2013.01); *A61K 2039/804* (2018.08); *C12Q 2600/156* (2013.01)

(58) Field of Classification Search
 None
 See application file for complete search history.

(56) References Cited

U.S. PATENT DOCUMENTS 8,623,647 B2   1/2014  Tebbi
9,783,785 B2  10/2017  Tebbi

FOREIGN PATENT DOCUMENTS

WO   WO 2012/087278 A1   6/2012

OTHER PUBLICATIONS

Tebbi et al (Cancer Treatment and Res. Comm., 26:100279, 2021).*

* cited by examiner

*Primary Examiner* — Brian Gangle
(74) *Attorney, Agent, or Firm* — Patent Technologies, LLC; Robert D. Gunderman, Jr.

(57) ABSTRACT

A method for detection and prevention of leukemia and lymphoma is disclosed. When mononuclear blood cells from an individual are exposed to a supernatant of a mycovirus-containing *Aspergillus flavus*, the degree and pattern of activation and upregulation or downregulation transcription factors are indicative of an individual's susceptibility to leukemia or lymphoma. Upon detection of observed transcription factors, preventive measures are provided to the individual. Preventive measures may include, for example, a vaccine, or may be provided upon detection of observed transcription factors with those individuals that are genetically susceptible to leukemia and lymphoma.

7 Claims, 8 Drawing Sheets

SYSTEM AND METHOD FOR THE DETECTION AND PREVENTION OF LEUKEMIA AND LYMPHOMA

CROSS REFERENCE TO RELATED PATENT APPLICATIONS

None

STATEMENT REGARDING FEDERALLY SPONSORED RESEARCH OR DEVELOPMENT

None

BACKGROUND OF THE INVENTION

1. Field of the Invention

The present invention relates generally to cancer, and more particularly to a system and method for the detection and prevention of leukemia and lymphoma.

2. Description of the Related Art

Presently, leukemia ranks as the fifteenth most common diagnosed human cancer and eleventh cause of death due to a malignant disorder and affects both sexes and all age groups. Acute lymphoblastic leukemia (ALL) has an incidence of 1.7 per 100,000 population per year, most commonly affects children, and represents 25-30% of all pediatric malignant disorders. Pre-B and B-cell ALL originate from the transformation of B cell progenitors. While a large portion of the B-cell acute leukemias are shown to have certain genetic changes and altered regulators of normal B-cell development such as IKZF1 and PAX-5, the exact mechanism by which transcription factors drive this transformation is not entirely clear. One theory suggests that alteration of the normal differentiation process may play a critical role in the development of this disease. Likewise, in T-cell ALL several transcription abnormalities have been reported.

Lymphomas originate in cells of the lymphatic system and include different types sharing some of the same characteristics. Non-Hodgkin's lymphoma (NHL) is a term used for certain types of lymphoma. These disorders while most often affecting adults, are also seen in children. NHL involves the lymphatic system including lymph nodes, lymphatic tissues, skin, and other organs, and can affect lymphatic drainage. This group of diseases affects the immune system, and thus have major consequences regarding defensive capabilities.

Transcription factors play a vital role in the normal lymphoid and myeloid cell development. The actions of transcription factors include the integration of external signals to gene expression, programs that reconstruct cellular physiology at a basic level, and an array of modifications. Experimentally and clinically, several transcription factors have been found to be altered in ALL, where often some of these factors are downregulated. Based on animal studies, graded reduction of lineage indispensable factors can induce leukemia.

Some of the transcription factors which are reported to be consequential in the process of promoting B cell differentiation include PAX-5, Ebf1 and Ikaros. These transcription factors, and others, form a network which promotes B cell differentiation. In pre-B cell ALL, often genes encoding some transcription factors are altered or deleted, indicating their role in this disease. It has been postulated that haploinsufficiency for PAX-5 or Ebf1 synergizes with STAT5 activation to initiate the process of the ALL development. Furthermore, a number of common genetic variants associated with increased risk for ALL have been recognized. In children with ALL, it is estimated that at least 4% are likely to have functional germline mutations. In familial ALL, predisposing germline mutations in the hematopoietic regulator genes PAX-5, SH2B3, ETV6, and Ikzf1, has been reported. Alteration in the Ikaros transcription factors also occurs in the T-cell acute lymphoblastic leukemia. It has been proposed that the etiology of ALL involves a combination of the genetic predisposition followed by a provoking event such as an infection.

Some mycoviruses are found to cause major changes such as reduced virulence, irregular growth, altered pigmentation, and sexual reproduction in their host. Certain mycoviruses are found to evoke transcriptional rewiring of their host organism. It appears that the expression level of specific host genes differs in mycovirus-free and infected fungus. Alterations in transcription factors in mycovirus infected fungi have been reported. Also, experimentally, transcriptome sequencing (RNA-seq) of mycovirus-infected *Malassezia sympodialis* has been reported to result in an upregulation of several ribosomal components as compared to virus-cured control, indicating that the mycovirus can modify the transcriptional and translational aspects of the host. Only very limited data regarding the effects of mycoviruses on human health is available.

The cause of leukemias and lymphomas has been largely unknown at the present time, and as such, detection of the underlying mechanisms behind this disease and associated preventive action has heretofore not been possible. An understanding of the mechanisms involved would therefore be a breakthrough innovation unto itself, and resulting systems and methods for the detection and prevention of this disease are therefore needed. The inventor has isolated a mycovirus-containing *Aspergillus flavus* to which, unlike controls, patients with acute lymphoblastic leukemia and lymphoma have antibodies detectable by enzyme-linked immunosorbent assay (ELISA) technique. In vitro exposure of mononuclear blood cells from patients with ALL in remission, and long-term survivors to the product of this organism, unlike controls, results in redevelopment of genetic and cell surface phenotypes characteristic of active leukemia. Further study of the products of this organism, which include the subject matter of the present invention, reveals that these products are capable of altering genetic changes in the cells. Such changes, demonstrated by the alteration of transcription factors, are different in normal and leukemic cells and are a basis for diagnostic methods and interventions described herein.

BRIEF SUMMARY OF THE INVENTION

In accordance with the present invention, there is provided a method for detection and prevention of leukemia and lymphoma, the method comprising the steps of obtaining mononuclear blood cells from healthy individuals or those suspected to have, or have acute lymphoblastic leukemia (ALL) in remission or lymphoma; exposing the mononuclear cells to a supernatant of a mycovirus-containing *Aspergillus flavus*; observing for activation and upregulation or downregulation transcription factors; determining the genetic susceptibility of the individual to leukemias and lymphomas; and providing preventive measures to the susceptible individuals upon detection of changes observed in the transcription factors. In some embodiments of the present invention, the preventive measures are provided if the individual is genetically susceptible to leukemias and lymphomas. In some embodiments of the present invention, the preventive measure is a vaccine.

The foregoing has been provided by way of introduction, and is not intended to limit the scope of the invention as described by this specification, claims and the attached drawings.

BRIEF DESCRIPTION OF THE DRAWINGS

The invention will be described by reference to the following drawings, in which like numerals refer to like elements, and in which:

FIG. 4 is a graph depicting effects of mycovirus-containing *Aspergillus flavus* on transcription factor Ikaros 75 kDa of various cell lines;

FIG. 5 is a graph depicting effects of mycovirus-containing *Aspergillus flavus* on transcription factor NF-kB p65 of various cell lines;

FIG. 6A depicts flow cytometry comparing Annexin V and a supernatant of mycovirus-containing *Aspergillus flavus;*

FIG. 6B depicts flow cytometry comparing Annexin V and a supernatant of mycovirus-containing *Aspergillus flavus;*

FIG. 7C depicts flow cytometry comparing Annexin V and a supernatant of mycovirus-containing *Aspergillus flavus;*

FIG. 7D depicts flow cytometry comparing Annexin V and a supernatant of mycovirus-containing *Aspergillus flavus;*

FIG. 8E depicts cell cycle analysis comparing exposure to the supernatant of *Aspergillus flavus* for 72 hours and control; and

FIG. 8F depicts cell cycle analysis comparing exposure to the supernatant of *Aspergillus flavus* for 72 hours and control.

The present invention will be described in connection with a preferred embodiment; however, it will be understood that there is no intent to limit the invention to the embodiment described. On the contrary, the intent is to cover all alternatives, modifications, and equivalents as may be included within the spirit and scope of the invention as defined by this specification, claims and drawings attached hereto.

DESCRIPTION OF THE PREFERRED EMBODIMENTS

The present invention, and the various embodiments described and envisioned herein, provide a method for the detection and prevention of leukemia and lymphoma.

The inventor has discovered that, using the enzyme-linked immunosorbent assay (ELISA) technique, patients with acute lymphoblastic leukemia (ALL) in full remission, and long-term survivors, have antibodies to the supernatant of the culture of a certain mycovirus-containing *Aspergillus flavus* (MCAF). The mycovirus may include one or more mycoviruses including, but not limited to, Endornaviridae, Chrysoviridae. Megabirnaviridae, Quadriviridae, Partitiviridae, Reoviridae, and Totiviridae. Multiple sets of controls, including normal individuals, patients with a variety of solid tumors and those with sickle cell disease lack such antibodies. It is of interest that the organism used in the studies of the inventor was isolated from the home of a patient with ALL. The isolated MCAF organism does not produce any aflatoxin which may be due to its infestation with a mycovirus. Mycoviruses are shown to suppress production of aflatoxin in their fungal host. The latter was attributed to the virus/virus and virus/host interactions that can block the production of aflatoxin. Studies of the inventor also have revealed that exposure of the mononuclear cells from ALL patients in full remission to the products of the MCAF results in the re-development of cell surface phenotypes and genetic markers, characteristic of ALL, while controls are negative. The findings related to *Aspergillus flavus* and leukemia and lymphoma are disclosed in U.S. Pat. Nos. 8,623,647 and 9,783,785 the entire disclosures of which are incorporated herein by reference. While the findings disclosed in the U.S. Pat. Nos. 8,623,647 and 9,783,785 patents were compelling, they were not sufficient to allow for the development of a genetic-based diagnostic and therapeutic, and preventive protocols such as those disclosed herein. The present invention employs the fact that the isolated *Aspergillus flavus* contains mycovirus. The prior U.S. Pat. Nos. 8,623,647 and 9,783,785 did not include the new discoveries, described herein, revealing that exposure to the products of MCAF alters the genetics, and specifically transcription factors in the exposed cells, which is the basis of the diagnostic techniques described herein.

The present invention, as disclosed herein, describes that products of the isolated organism alter transcription factors and their utility in detecting, preventing and treating leukemia and lymphoma. For example, a method for detection of susceptibility to leukemia and lymphoma in accordance with the present invention comprises the steps of obtaining hematopoietic mononuclear cells from healthy individuals or those susceptible or suspected to have acute lymphoblastic leukemia (ALL) or lymphoma or patients in remission; exposing the mononuclear cells to a supernatant of a mycovirus-containing *Aspergillus flavus*; evaluating the pattern and degree of upregulation or downregulation of transcription factors and providing preventive action to the individuals upon detection of changes in the observed transcription factors. The preventive action may, in some embodiments, be a vaccine. The vaccine, for example, provides for the production of antibodies specific to a mycovirus-containing *aspergillus* species. In some embodiments of the present invention, the preventive action includes blocking the development of new pathways which would otherwise enhance the development of acute lymphoblastic leukemia (ALL). In some embodiments, the genetic changes include but are not limited to alterations in the NF-kB, PAX-5, IKAROS 55 kD and 75 kD transcription factors. In some embodiments, a method for prevention of leukemia and lymphoma comprises the step of removing DNA specific to a mycovirus associated with *Aspergillus Flavus* from a host cell genome. The host cell genome, for example, may be from the host cell of a human or animal.

In some embodiments of the present invention, the preventive action is administered if the individual is genetically susceptible to leukemias and lymphomas. Examples of genetic changes include but are not limited to alterations in the NF-kB, PAX-5, IKAROS 55 kD and 75 kD transcription factors.

Transcription factors control and regulate cellular genetic expressions and can alter the functions of cells by modulating the nature and rate of gene transcriptions. The role and changes in the expression of several transcription factors in acute lymphoblastic leukemia (ALL) are well recognized. Currently, information regarding the effects of various environmental and external influences on transcription factors is limited. It is known that mycoviruses, as a part of their cytopathogenesis, have the ability to alter the genetics of their fungal host and transform its biological characteristics and functions. The present invention and research associated therewith evaluate the effects of the products of a certain mycovirus containing Aspergillus flavus (MCAF), which was initially isolated from the home of a patient with ALL, on the transcription factors of ALL cell lines and controls. Patients with B-cell ALL have antibodies to MCAF and exposure of the mononuclear leukocytes of patients in complete remission to its products, unlike controls, results in the re-development of genetic and cell surface phenotypes characteristic of ALL. For one study performed by the inventor, which is a basis of the present invention, pre-B and B-cell lines were exposed to incremental doses of the products of the culture of mycovirus containing Aspergillus flavus (SMCAF), Controls were normal, T-cell ALL and chronic myelogenous leukemia (CML) cell lines. Before and after exposure to SMCAF, using immunoblotting technique, the levels of PAX-5, NF-κB (p65), Ikaros (75 kDa and 55 kDa) and NF-κB transcription factors were assessed. Cellular viability and cell cycle changes were also evaluated. After exposure to SMCAF, a significant difference between the normal and leukemia cell line was detected. Exposure of normal cell line to the SMCAF resulted in apoptosis, changes in cell cycle and downregulation of all tested transcription factors, to the extent that with the higher doses used, no levels were detectable. In acute leukemia cell lines, cell death and changes in the cell cycle were also noted, however, while there was downregulation of all tested transcription factors, in a dose-dependent manner, even with the highest doses used, these retained some levels of all transcription factors. No statistically significant downregulation of NF-κB in the CML cell line was noted. Culture media used as control had no effects. The noted alterations are of significance since mutation, suppression and dysfunction of transcription factors can result in deregulation and dysfunction of targeted cells and can affect cellular transformation and can cause proliferation abnormalities, leading to malignant disorders. Aspergillus species are widespread in nature and can contain mycoviruses, which are known to alter genetics of their hosts. The role of mycoviruses, with and without their fungal host, has been, and continues to be, studied and researched by the present inventor, with the results being used to create the present invention and the various embodiments described and envisioned herein.

The following studies by the inventor were designed to evaluate if the supernatant of a mycovirus-containing Aspergillus flavus (SMCAF) has any effects on the cellular transcription factors of leukemia and normal control cell lines. These investigations also examine the effects of the SMCAF on the cell survival rate, and cell cycle of established pre-B and B-cell ALL cell lines, compared to the normal B-lymphocyte, T-cell leukemia and chronic myelogenous leukemia cell lines.

Mycovirus-containing Aspergillus flavus: This organism was initially isolated from the home of a patient with ALL, was cultured in an underlayer of 1% solid agar with an overlayer of 3.5% Czapek-Dox broth (Difco; Becton Dickinson, Sparks, MD, USA) in a glass bottle, incubated at 28° C. and sub-cultured at approximately four weeks intervals. To assure persistence of the mycovirus in the Aspergillus flavus, the cultures were periodically checked for existence of mycoviruses by transmission electron microscopy. For the described studies, a portion of the supernatant of mycovirus-containing Aspergillus flavus was collected after approximately four weeks of culture, filtered through 0.45 μm filter (Thermo Sci. Catalogue #169-0045), and concentrated via a centrifugal filter device with 3K of nominal molecular weight limit (NMWL) (Amicon Ultra-15 centrifugation device, EMD Millipore, EMD Millipore Corporation, Taunton, MA, USA) at 4.000×g for 55 min. The concentrated SMCAF was quantitated by BCA protein assay kit (ThermoFisher Scientific, Pittsburgh, PA, USA) and had an approximately total protein concentration of 3-4 mg/ml.

Chemical evaluation: The supernatant of culture of mycovirus-containing Aspergillus flavus was repeatedly tested to assure that it is free of aflatoxin.

Cell lines: Cell lines used were originally obtained from Coriell Institute for Medical Research (Camden, NJ, USA). The pre-B and B-cell ALL cell line were GM20390 and NALM-6 clone G5 (CRL-3273), respectively. For comparison, RPMI-1788, a normal cell line, BCL2 Jurkat, an acute T-cell lymphoblastic leukemia cell line and K562-S(CRL-3343), a chronic myelogenous leukemia (CML) cell line, were used. All cell lines were cultured in RPMI-1640 (Thermo Fisher Scientific, Waltham, MA, USA) with 10% fetal calf serum (Thermo Fisher Scientific, Waltham, MA, USA) and Penicillin/Streptomycin antibiotics and incubated at 37° Centigrade with 5% CO2. Cells were harvested, counted, adjusted and seeded at $2.4 \times 10^4$/ml for culture. For the described studies, each cell line was cultured for 3 days with concentrated SMCAF using 0.1, 0.2, 0.3 and 0.4 mg protein per milliliter. Culture media was used as control. Upon harvest, cell count and viability test for each culture was performed. For measurement of cell viability rate, pre and 72 hours post treatment of each cell line that were cultured with SMCAF stained with methylene blue and counted using a hemocytometer. Percentage of survival was recorded.

Electron microscopy: To evaluate the Aspergillus flavus for the presence of mycoviruses, both the fungal growth and supernatant of the culture were analyzed for viral contents by electron microscopy. The grown organism was fixed in glutaraldehyde and osmium tetroxide. This was placed into resin blocks suitable for ultramicrotomy sectioning at 70 nm, collected on copper grids and contrast-enhanced with uranyl acetate before transmission electron microscopy observation.

Cell cycle studies: To characterize the effect of the SMCAF on the cells, cell cycle analysis studies were performed. Cells were washed and resuspended in 200 μl of PBS, followed by the dropwise addition of 2 ml ice cold 70% ethanol during vortex mixing. The cell suspension was incubated at −20 degree Centigrade for two hours. The cells then were washed with PBS and resuspended in 400 μl of staining solution containing 0.6 mM of Propidium Iodide (PI) (Invitrogen P3566, Invitrogen, Carlsbad, CA, USA), 0.2 mg/ml of RNAse (ThermoFisher, R1253. ThermoFisher Scientific, Pittsburgh, PA, USA) and 0.1% v/v of TRITON™ X100 (ThermoFisher, BP151-100, ThermoFisher Scientific, Pittsburgh, PA, USA). Cells were incubated at 37 degrees Centigrade for 30 minutes before measurement of fluorescence using a BD® LSR II (BD Bioscience, Franklin Lakes, NJ, USA) flow cytometer. Data was analyzed using FLOWJO™ software (Tree star Watson model. Tree Star, Inc., San Carlos, CA).

Annexin V/PI analysis: To examine the apoptotic cell death, cells were seeded at $2\times10^5$/well in a T75 flask in RPMI 1640 media with 10% fetal calf serum and 1% Penicillin/Streptomycin and incubated at 37° Centigrade with 5% $CO^2$. The cells were treated with SMCAF with protein concentrations as outlined above. Cultures were collected after 72 hours of incubation. Cells were resuspended in 100 ul of Annexin V binding buffer (component no. 51-66121E, BD Biosciences, San Diego, CA, USA) with 5 ul of Annexin V-FITC (component no. 556419, BD Biosciences, San Diego, CA, USA) and incubated for 15 minutes at room temperature. At this point, 200 ul of Annexin V staining buffer were added and fluorescence was measured using an LSR II flow cytometer (BD Biosciences. San Diego, CA, USA) and data was analyzed using FlowJo software (Tree Star, Inc., San Carlos, CA, USA). Annexin V positive, PI negative cells were identified as early apoptotic while Annexin V positive, PI positive cells were identified as late apoptotic.

Western Blot: The levels of transcription factors PAX-5, Ikaros 55 kD and 75 kD and NF-κB p65 were measured, with and without exposure to SMCAF, using immunoblotting. For Western blot, each cell line was harvested, centrifuged at 2000 RPM at 20° C. for five minutes, and the pellets were washed twice with 4 ml of ice-cold Tris-Buffered saline (TBS) (ThermoFisher Scientific, Pittsburgh, PA, USA). Cells were treated with specified amount of SMCAF, as described above, or culture media which was used as control. Radio-Immune Precipitation Assay (RIPA) lysis buffer (ThermoFisher Scientific, Pittsburgh, PA, USA) was used at final concentration of $3\times10^7$ cells/ml. The RIPA consisted of 50 mM Tris-HCl (pH 7.4). 1.0% NP-leupeptin and pepstatin (ThermoFisher Scientific, Pittsburgh, PA, USA). Each cell lysate was mixed on a shaker for 15 minutes at 4° Centigrade, sonicated twice for 10 seconds at 50 kHz, shaken for 15 minutes on ice, and then centrifuged at 12000 g at 4° Centigrade for 20 minutes. The total protein was measured using BCA assay, aliquoted in 10 μg/μl in the loading buffer and then denatured at boiling water for five minutes before being subjected to the Western blot analysis. To perform protein electrophoresis, the precast Mini Tris Glycine gel 4-20% (Bio-Rad, Hercules, CA, USA) was utilized. For protein transfer a 0.22 μm nitrocellulose membrane and Efficient western transfer buffer (Bioscience. St Louis, MO, USA) were used. For the membrane blocking, 5% dry milk in 1×TBST wash buffer (tris-buffered saline with 0.05% polysorbate 20) was utilized. To detect transcription factors Ikaros, NF-κB p65 and PAX-5 appropriate primary monoclonal antibodies and the secondary antibody HRP-linked anti-rabbit IgG were used (Cell Signaling Technology, Danvers, MA, USA). The antibody binding was detected by the enhanced chemiluminescence system (Viagene Biotech, Tampa, FL, USA) and read on FlourChem E system (ProteinSimple, San Jose, CA, USA). The Western blot images were analyzed with ImageJ software. Each study was repeated four times and statistical studies were done based on these repeats. For statistical analysis, two-tailed t-test was used and P values<0.05 were considered significant.

Results

The results from the studies described herein and which are the basis of the present invention are as follows:

Chemical analysis: Evaluation of the supernatant of the culture of mycovirus-containing *Aspergillus flavus* revealed that this organism does not produce any aflatoxin.

Figure 1:
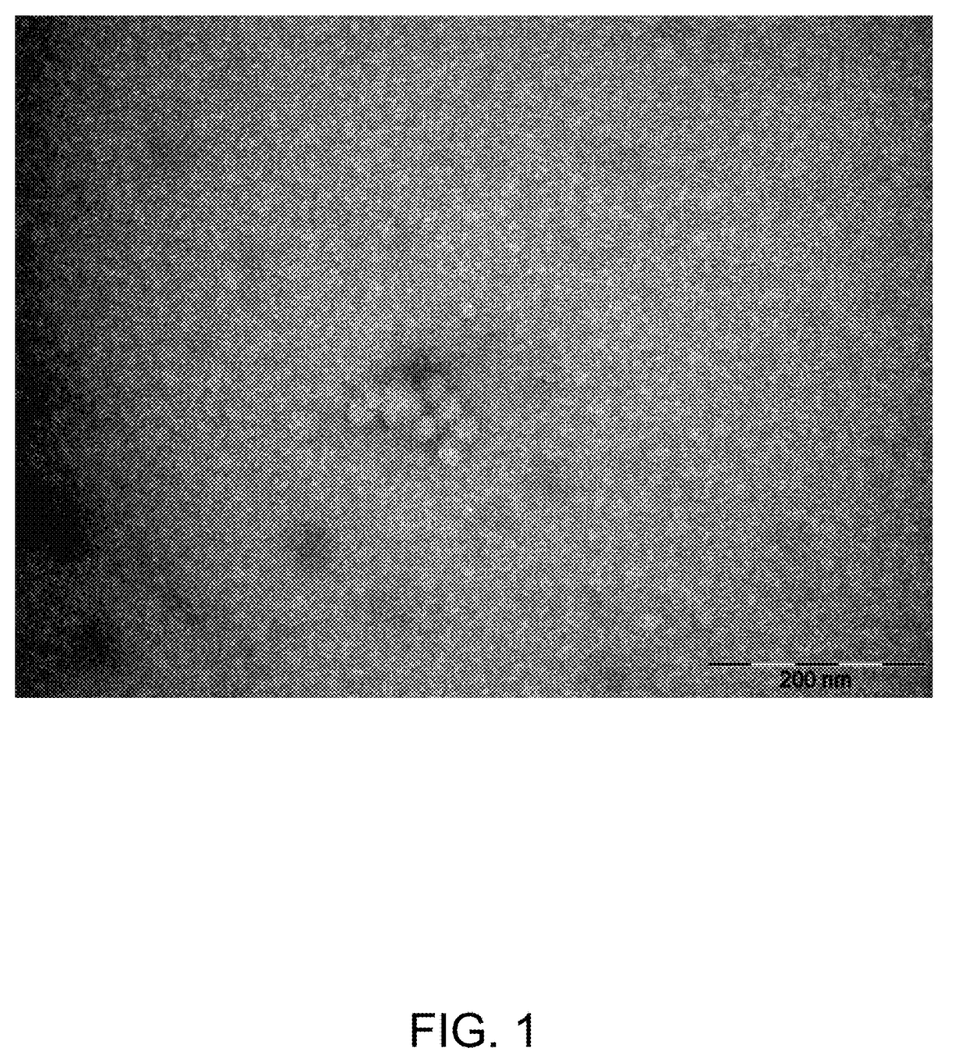
FIG. 1 is a transmission electron microscopy image of viral particles from a culture of *Aspergillus flavus*.

Electron microscopy: Transmission electron microscopy examination of the culture of *Aspergillus flavus* demonstrated existence of the virus-like particles within the body of the organism and the culture supernatant. In FIG. 1, viral particles were seen measuring 40 nm in diameter in the transmission electron microscopy evaluation of the culture of *Aspergillus flavus* isolated from the home of a patient with acute lymphoblastic leukemia. The sample was collected from the suspension culture of *Aspergillus flavus* and was glutaraldehyde fixed. Transmission electron microscopy is a micrograph using formvar-coated copper grid preparation, contrast-enhanced with aqueous uranyl acetate.

The sizes of the particles observed ranged between 30-50 nm and were in single or aggregate form, with or without patent dense cores. Particles ranging from 20-25 nm and 60-80 nm containing dense cores were seen in the hyphae.

Figure 2:
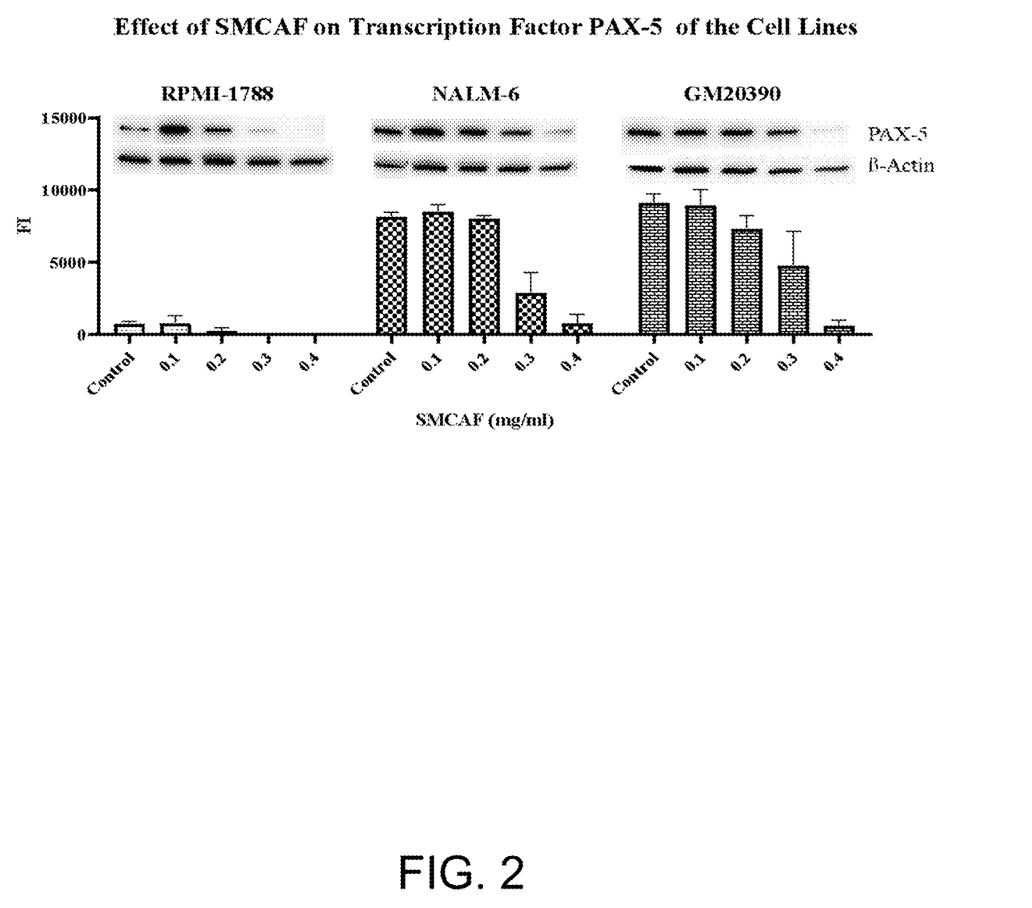
FIG. 2 is a graph depicting effects of mycovirus-containing *Aspergillus flavus* on transcription factor PAX-5 of various cell lines.

Transcription factors: In the RPMI 1788 cell line, which was used as a normal control, addition of SMCAF resulted in a dose-dependent downregulation of all transcription factors tested i.e., PAX-5, Ikaros 55 KD and 75 kD and NF-κB p65. No detectable levels remained with the dose of 0.4 mg/ml (p<0.01). (see FIGS. 2-5). In the pre-B and B-cell lines, a dose-dependent downregulation of PAX-5 in NALM6 clone G5 (CRL-3273) and GM20390 cell lines were noted (see FIG. 2). FIG. 2 depicts the effects of mycovirus-containing *Aspergillus flavus* on normal control (RPMI-1788), pre-B (NALM-6) and B-cell (GM20390) cell lines. While downregulation of PAX-5 transcription factor normal cell line is complete with no residual remaining, this is significantly less and incomplete in the pre-B and B-cell lines.

The pattern in the downregulation of PAX-5 was similar in the NALM-6 and GM20390, a pre-B and B-cell leukemia cell lines. (see FIG. 2). However, unlike RPMI-1788, where with doses of greater than 0.2 mg/ml of SMCAF there was a complete abolition of this transcription factor, in GM20390 and NALM-6 cell lines, with the dose of 0.2 mg/ml, a statistically insignificant downregulation of PAX-5 was noted (p=0.23 and 0.65, respectively) (FIG. 2). However, even with doses of 0.4 mg/ml, while a statistically significant downregulation occurred (p=0.006 and <0.0001, respectively), still a residual PAX-5 transcription factor could be detected (see FIG. 2).

Figure 3:
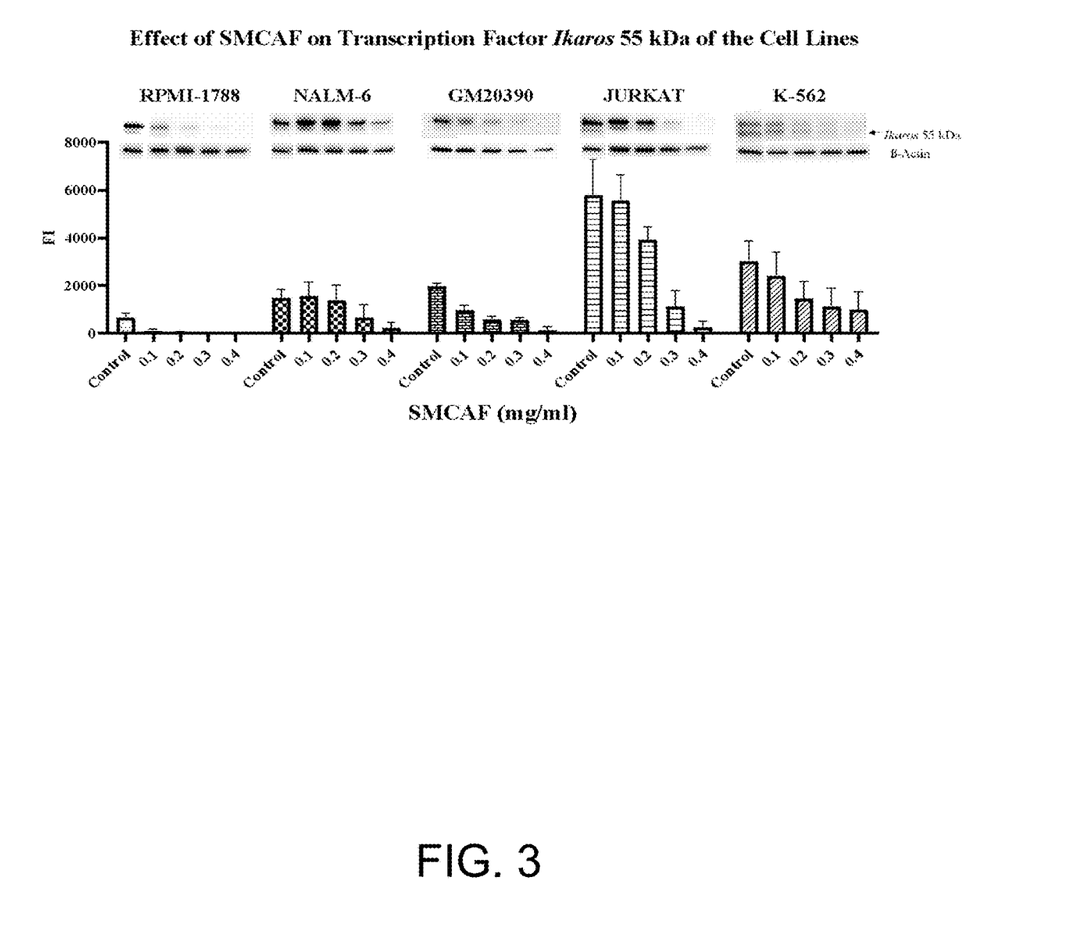
FIG. 3 is a graph depicting effects of mycovirus-containing *Aspergillus flavus* on transcription factor Ikaros 55 kDa of various cell lines.

FIG. 3 depicts the effects of mycovirus-containing *Aspergillus flavus* on normal control (RPMI-1788), pre-B (NALM-6), B-cell (GM20390), T-cell (JURKAT) and K-562 (CML) cell lines. While downregulation of Ikaros 55 kD transcription factor in normal cell line is complete with no residual remaining, this is significantly less and incomplete in the pre-B, B-cell, T-cell and CML cell lines.

Evaluation of the effects of SMCAF on the Ikaros 55 kD transcription factor in NALM-6 and GM20390 revealed that the downregulation was gradual and incomplete (see FIG. 3).

With the highest dose used, this downregulation remained incomplete. This is in contrast with RPMI-1788, a normal cell line, where statistically significant downregulation of Ikaros 55 kD was noted with addition of 0.1 mg/ml (p=0.034) and with doses greater than 0.2 mg/ml no residual of this transcription factor was detected. In the NALM-6 cell line, with the doses of 0.1 to 0.3 mg/ml of SMCAF, downregulation of Ikaros 55 kD was not statistically significant (p=0.9165, 0.8946 and 0.2725 respectively), however, with a dose of 0.4 mg/ml, the changes became significant, but incomplete (p=0.0411). In the GM20390 cell line, with doses of 0.1-0.4 mg/ml of the SMCAF, a gradual, but incomplete, downregulation of Ikaros 55 kDa was noted (p=0.0436, 0.0148, 0.0103, and 0.0091 respectively). (see FIG. 3). A similar finding was observed on the effects of SMCAF on Ikaros 75 kD on pre-B and B-cell lines, albeit with more gradual downregulation of this transcription factor. In Nalm-6 and GM20390, statistically significant downregulation of Ikaros 75 kD were found with the addition of 0.2 and 0.3 mg/ml of SMCAF (p=0.5787 and 0.0447 for Nalm-6; p=0.0184 and 0.0238 for GM20390, respectively). RPMI 1788 used as control had statistically significant downregulation of Ikaros 75 kD with the dose of 0.1 mg/ml and with dose of greater than 0.2 mg/ml no residue of this factor was 19 detectable (see FIG. 4).

Figure 4:
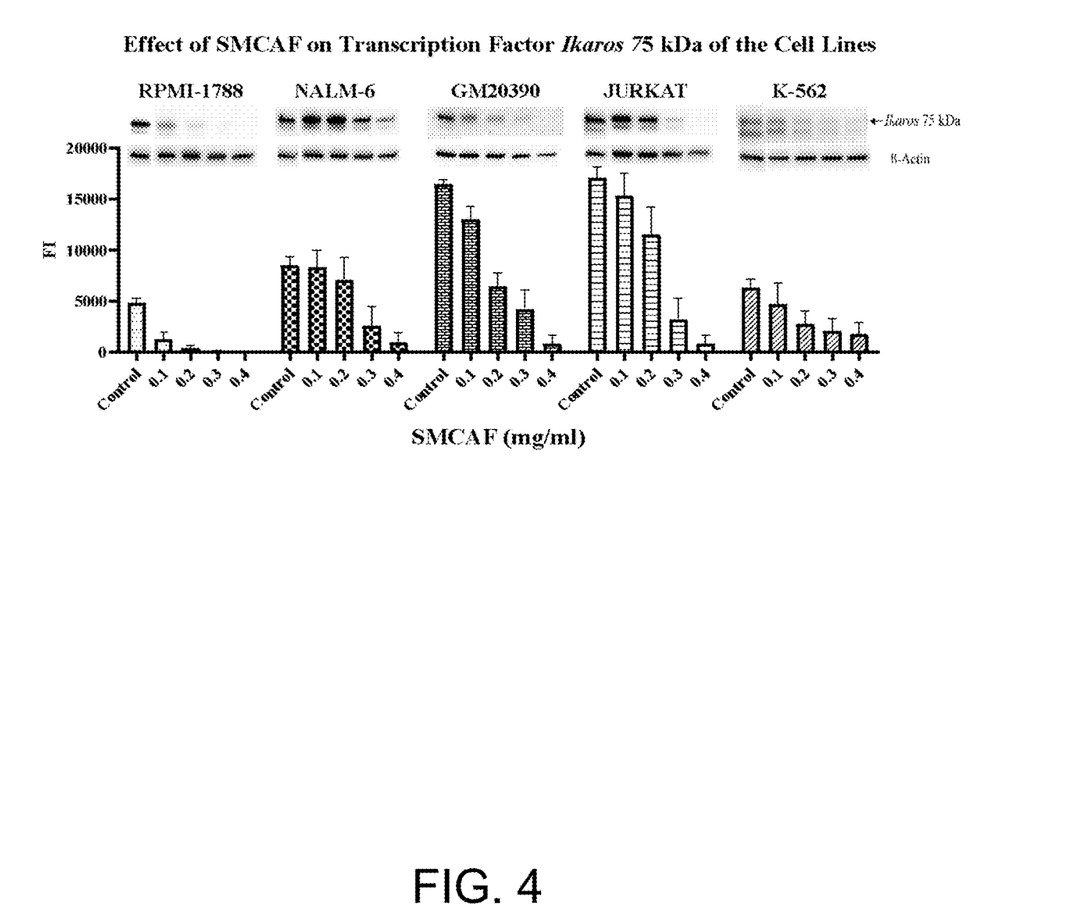

FIG. 4 depicts the effects of mycovirus-containing *Aspergillus flavus* on normal control (RPMI-1788), pre-B (NALM-6). B-cell (GM20390), T-cell (JURKAT) and K-562 (CML) cell lines. While downregulation of Ikaros 75 kD transcription factor in normal cell line is complete with no residual remaining, this is significantly less and incomplete in the pre-B, B-cell, T-cell and CML cell lines.

Figure 5:
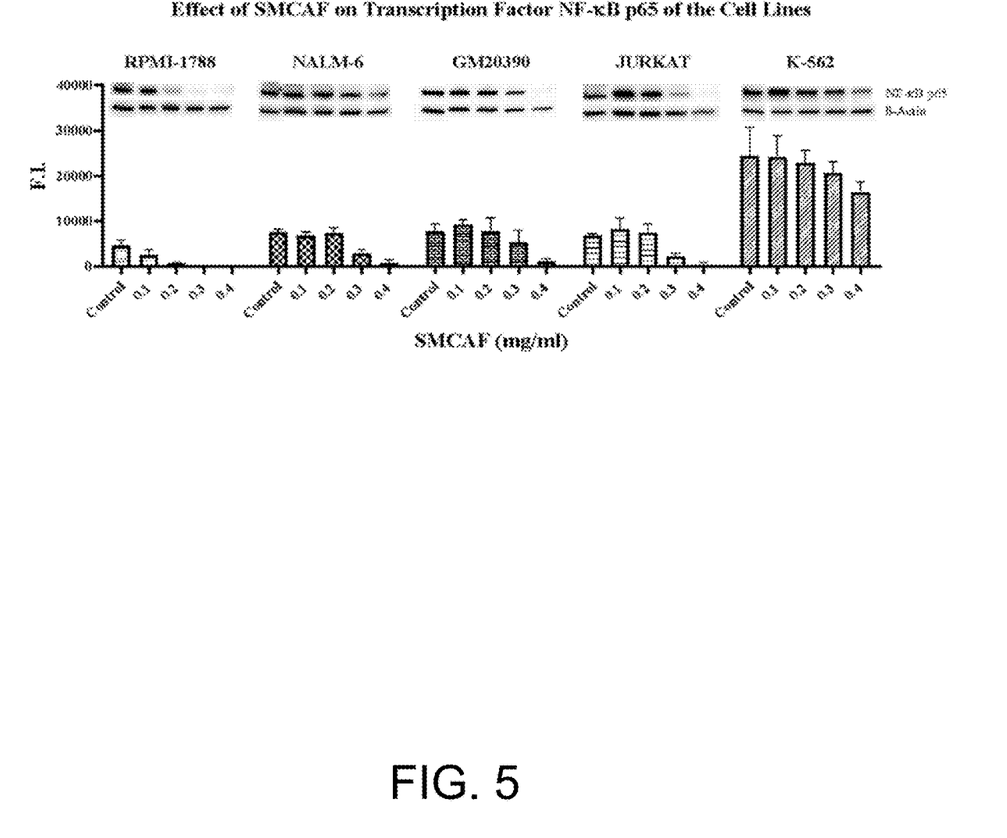

Exposure of RPMI-1788 to SMCAF, resulted in the downregulation of transcription factor NF-κB p65 to the extent that with SMCAF doses of greater than 0.2 mg/ml no levels were detectable (p=0.0204). The effects were less in the pre-B cell Nalm-6 cell line where the levels of this transcription factor significantly decline only with SMCAF doses of 0.3 and 0.4 mg/ml (p=0.0014 and p<0.0001 respectively). No significant changes of NF-κB found in GM20390 cells with any doses of SMCAF ranging from 0.1 to 0.4 mg/ml was noted (p=0.5193, p=0.9831, p=0.3000 and p=0.0625 respectively) (see FIG. 5). FIG. 5 depicts the effects of mycovirus-containing *Aspergillus flavus* on normal control (RPMI-1788), pre-B (NALM-6), B-cell (GM20390), T-cell (JURKAT) and K-562 (CML) cell lines. While downregulation of NF-κB P65 p65 transcription factor in normal cell line is complete with no residual remaining, this is significantly less and incomplete in the pre-B, B-cell, T-cell cell lines. In CML cell line no statistically significant reduction in the NF-κB P65 transcription factor was noted.

The control cell lines, Jurkat and K562, do not have PAX-5 transcription factor. In the Jurkat cell line, upon exposure to the SMCAF, transcription factor Ikaros 55 kD slowly downregulated, however with doses of 0.1 to 0.2 mg/ml this was not significant (p=0.9016 and 0.3031 respectively). With the dose of 0.3 and 0.4 mg/ml, a significant downregulation was noted (p=0.0453 and p=0.0214 respectively). The transcription factor Ikaros 55 kD in K-562 cells showed no significant changes with any doses of the SMCAF used. A similar pattern for Ikaros 75 kD was noted in the Jurkat cells. Addition of SMCAF resulted in very gradual downregulation of the transcription factor Ikaros 75 kD with doses 0.3 and 0.4 mg/ml used, respectively (p=0.0037 and p=0.0003). Similarly, the Ikaros 75 kD level in K562 cell line was gradually but significantly downregulated with the SMCAF doses of 0.3 and 0.4 mg/ml (p=0.0425 and p=0.0313). Downregulation of NF-κB p65 in the Jurkat cell line was only significant with the SMCAF doses of 0.3 and 0.4 mg/ml (p=0.0051 and p=0.0003). In K-562 cell line, with all SMCAF doses used, the NF-κB p65 level was not significantly altered (p>0.29) (see FIG. 5).

Culture media used as a control for SMCAF had no significant effects on the levels of all transcription factors in all cell lines tested (see FIGS. 2-5).

Figure 6:
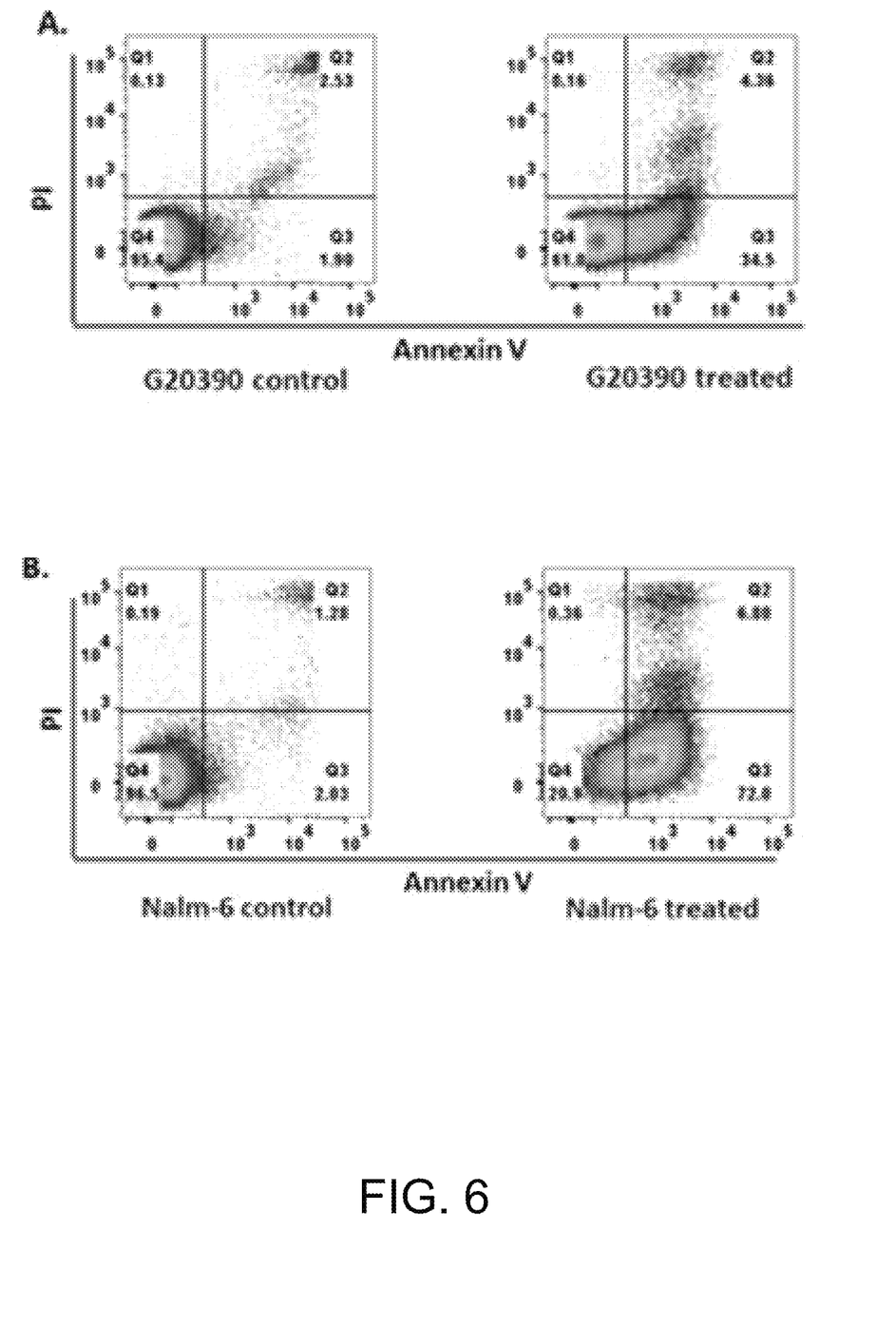
Figure 7:
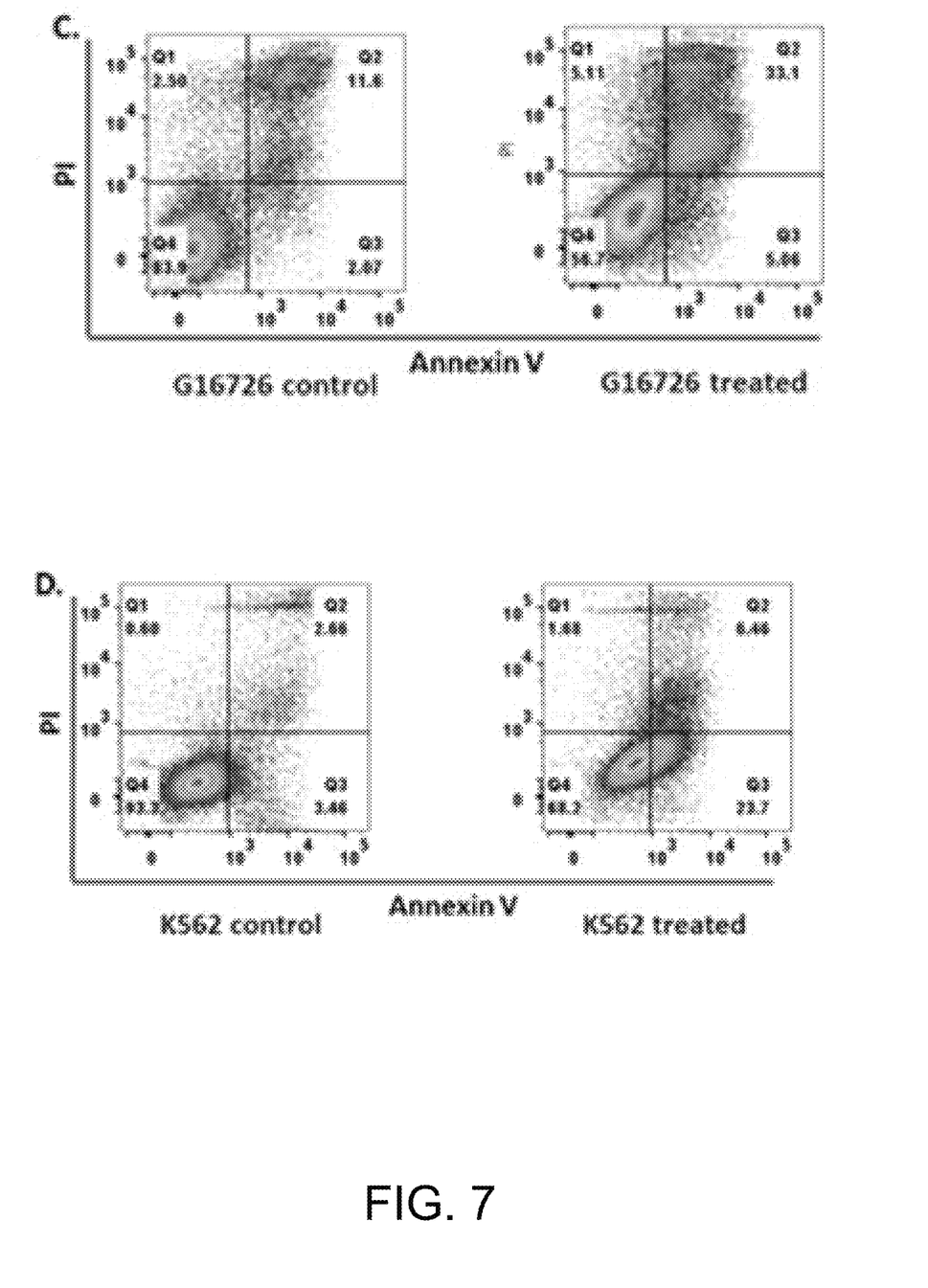
Figure 8:
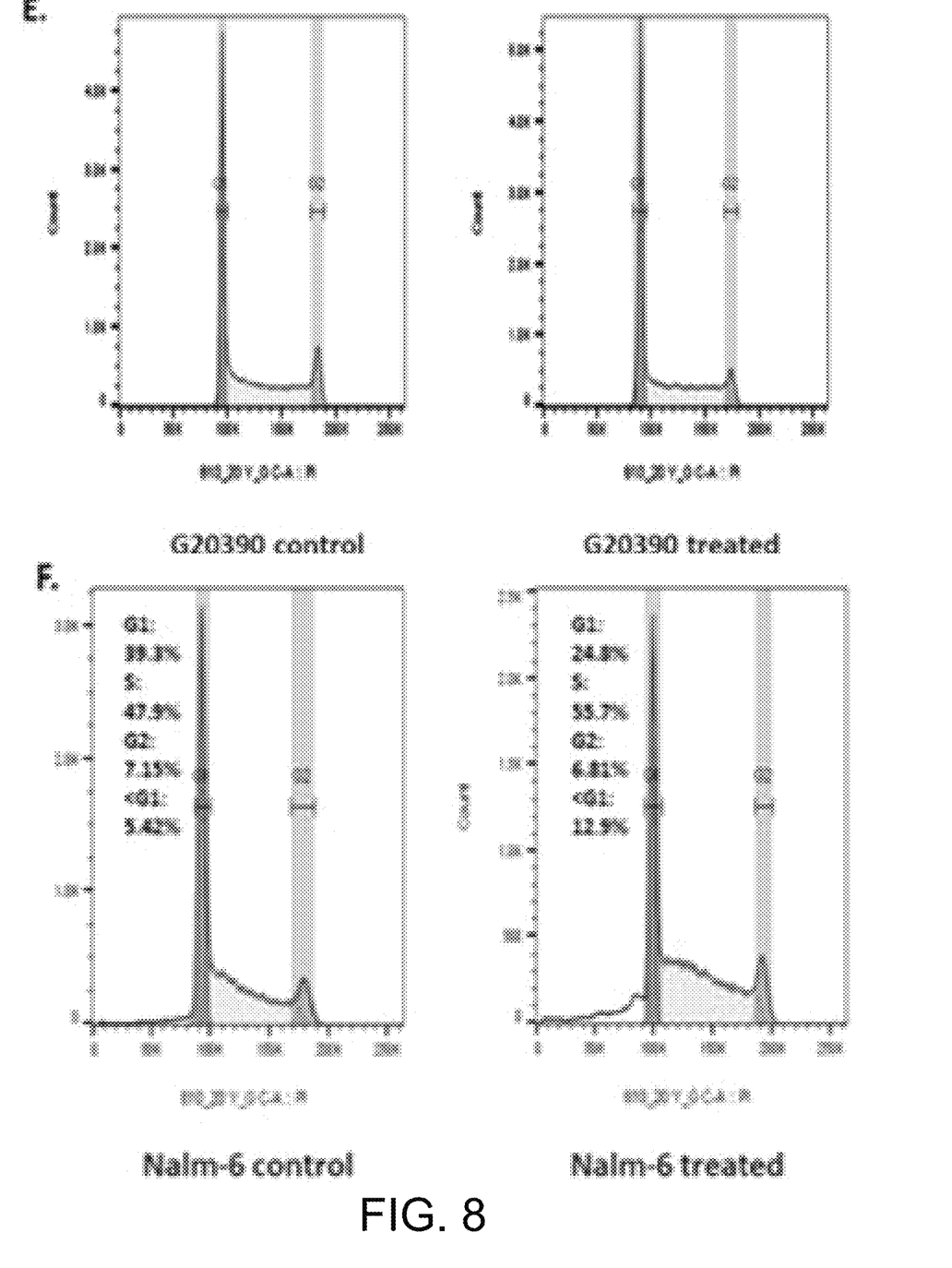

Apoptosis and cell cycle: Upon exposure to SMCAF, analyses revealed notable changes in the leukemic cell lines. The results of the apoptosis studies, done with AnnexinV/PI staining, revealed that there is a significant increase in the early apoptosis in the GM20390 and Nalm-6 cell lines after 72 hours of treatment with the SMCAF (see FIG. 6A-B). FIG. 6 depicts the effects of the SMCAF on the apoptosis and cell cycle of leukemic cell lines. (A-D) Annexin/PI analysis and (E-F) cell cycle analysis of leukemic cells after 72 hours treatment with SMCAF.

In addition, a significant increase in late apoptosis was observed in the cell line GM16726 after such a treatment (see FIG. 6C). In K562 cell line an increase in early apoptosis was also observed. Cell cycle analysis was performed after 72 hours of the supernatant of the culture of mycovirus-containing *Aspergillus flavus* treatment. Cell cycle analysis was performed after 72 hours of the supernatant of the culture of mycovirus-containing *Aspergillus flavus* treatment. An increase in G1 phase was observed in the GM20390 cell line (33.9% to 41.6%) (see FIG. 6A). In addition, an increase in the S phase was noted in Nalm-6 (47.9% to 55.7%) cell line (see FIG. 6B). No changes were observed in the control cell lines (data not shown). Corroboration of apoptotic cell death was observed while analyzing for cell cycle in the increase of cells in G0 after treatment with the supernatant of the culture of mycovirus-containing *Aspergillus flavus* in Nalm-6 Jurkat cells.

These findings have been used to conceive and develop the present invention. Normal development and maintenance of hematopoietic system requires activity of several signaling pathways and transcription factors. These factors recognize and bind to specific DNA sequences and can control chromatin and transcription resulting in a system which guides genomic expression. Transcription factors are essential in the regulation of cellular growth and development of the hemopoietic cells. Chromosomal translocations and their aberrant expression can potentially be associated with leukemogenesis. Transcription factors are shown to have a role in cancer cell cycle, progression, metastasis, and resistance to treatment. Our findings indicate that exposure to mycovirus-containing *Aspergillus flavus* is capable of altering these transcription factors. In the described experiments, such exposure also resulted in cellular apoptosis and alteration of the cell cycle. These findings may indicate that a mycovirus-containing organism has the potential to modulate the rate of gene transcription, altering cellular division, proliferation, differentiation, metabolism, function and apoptosis. Changes in the transcription factors were not uniform and the effects significantly differed in normal as compared to leukemia cell lines. Even within the leukemia cell lines, significant differences in acute and chronic leukemias were noted. In the RPMI-1788, which was used as a normal control, exposure to low doses of SMCAF resulted in the downregulation of all transcription factors tested, to the point of non-detection. In contrast, with the highest dose utilized, still some transcription factors were detectable in all leukemia cell lines. Of interest is that in the latter, the effects varied based on the type of the transcription factor, and acute versus chronic leukemia cell lines. In the chronic myelogenous leukemia cell line, K-562, which was used as a control, even with the highest doses of SMCAF used, still transcription factors were significantly detectable, and in case of NF-κB p65, downregulation with all doses used was not statistically significant.

Downregulation of PAX-5, in pre-B and B-cell lines, was only seen with much higher doses of SMCAF as compared to RPMI-1788, a normal control. Other controls used, Jurkat and K562-S(CRL-3343) cell lines do not have any PAX-5 transcription factor. In the pre-B and B-cell leukemia cell lines, with doses of 0.1-0.2 mg/ml, statistically significant downregulation was not noted, and even with the highest dose of SMCAF, this transcription factor was still detectable. Located on chromosome 9 p13, PAX-5 acts as a transcriptional activator or repressor of the genes involved in the B lineage development. PAX-5 functions as a master regulator and as a factor for IgH locus rearrangement. In addition, it inhibits the differentiation toward other lineages. CD19 expression that occurs in the later stages of B-Cell development is entirely controlled by this transcription factor. Alteration and loss of the PAX-S transcription factor is suggested to contribute to leukemogenesis. Loss-of-function mutations in PAX-S transcription factor occur in B-progenitor acute lymphoblastic leukemia. In childhood B-cell progenitor acute lymphoblastic leukemia, genome-wide analysis using oligo SNP arrays. PAX-5 was found to be the main target of somatic mutations, being altered in 38.9% of the cases. In one adult study of this disorder, PAX5 was found to be mutated in 34% of patients. The mutation results in reduced levels of PAX-5 protein or generation of hypomorphic alleles. This is due to a partial rather than complete loss of function of this transcription factor. In some studies. PAX-5 fusion product, P5-C20orf112, is reported to induce downregulation of pre-B cell receptor genes and cause differential proliferation patterns in B-cell lymphoblastic cell lines. PAX-5 is shown to be involved in several leukemia-associated rearrangements, resulting in the fusion genes encoding chimeric proteins that antagonize PAX-5 transcriptional activity. It is shown that individuals with loss-of-function variants and those with somatic deletion of the wild type of PAX-5 allele can develop ALL.

In a reported study of a murine model, transgenic RNAi was used to reversibly suppress endogenous PAX-5 which cooperates with activated signal transducer and activator of transcription 5 (STAT5) to induce B-ALL. In this model, restoration of endogenous PAX-5, even on a temporary basis, had reversed the process, allowing surface expression of mature B cell markers and release of the pre-B stage differentiation block. This and similar studies have established a causal relationship between the PAX-5 and development of pre-B ALL. This mutation results in reduced levels of PAX5 protein or generation of hypomorphic alleles. In view of the reports that indicate alterations in PAX-5 transcription factor can result in leukemogenesis, our finding that exposure to SMCAF results in the downregulation of this transcription factor is of significance In the described studies, Ikaros transcription factors were tested in all cell lines since these are essential regulators of lymphopoiesis and are known to be involved in in ALL. Upon exposure to the products of MCAF, downregulation of Ikaros 55 kD/Ikaros 75 kD were noted to occur in all cell lines tested. In RPMI-1788, a normal cell line, the downregulation of Ikaros 55 kD and 75 kD were statistically significant with addition of 0.1 mg/ml or greater amount of SMCAF. Higher doses resulted in the total elimination of these transcription factors (FIGS. 3 and 4). Downregulations in the leukemia cell lines were less intense, and even with the 0.4 mg/ml, which was the largest dose used, were incomplete. In the pre-B and B-cell lines, downregulation of Ikaros 55 kD occurred after exposure to doses greater than 0.1 and 0.4 mg/ml of SMCAF respectively. Likewise, statistically significant downregulation of Ikaros 75 kD were found with 0.2 and 0.3 mg/ml of SMCAF. In these cell lines, Ikaros 55 kD, and more noticeably. Ikaros 75 kD, transcription factors were still detectable even with 0.4 mg/ml, which was the highest dose used. Effect of SMCAF on the JURKAT, and K-562 cell lines was less intense than the pre-B and B-cell lines and did not result in the total elimination of the Ikaros 55 kD and 75 kD transcription factors, with a significant residual detectable with the highest dose utilized.

The described studies reveal that products of mycovirus-containing *Aspergillus flavus* can alter and downregulate Ikaros 55 kDa and 75 kDa is of significance. Ikaros, a zinc finger transcription factor, is a major regulator of hematopoiesis and is frequently deleted or mutated in B-cell precursor acute lymphoblastic leukemia. Somatic mutations or alteration of Ikzf1 is seen in 15-20% of childhood B-cell ALL, and its deletion in over 75% of BCR-ABL positive disease. Ikzf1 mutations occur in up to approximately 50% of adult ALL. The mechanisms involved in Ikaros regulation of the gene expression and cellular proliferation in T-ALL are unknown. It has been shown that reintroduction of Ikaros into Ikaros-null T-ALL cells result in the termination of cellular proliferation and induction of T-cell differentiation.

Ikaros transcription factors are critical regulators of lymphocyte ontogeny and differentiation. During the process of hematopoiesis, Ikaros functions as a transcriptional activator or repressor for B and T cell differentiation via recruitment of chromatin remodeling complexes. The IKZF1 gene encodes the Ikaros protein, which is a regulator of hemopoiesis, and is particularly important in the development of all lymphoid lineages and also function as a tumor suppressor. Ikaros has a major regulatory function in B cell lymphopoiesis and in its transcription as a repressor through chromatin modification, co-repressor recruitment, and competition. Mutations of Ikzf1 are found in human B and T cell lymphoma and leukemia. The malfunctioning due to the loss of Ikaros activity potentially can contribute to the development of acute lymphoblastic leukemia. Individuals with Ikzf1 missense mutations who develop combined immunodeficiency syndrome can also present with multiple hematopoietic abnormalities including those of T. B, myeloid, and dendritic cell lineages. Those with a germline truncating variant in Ikzf1 (p.D186fs), have been reported to develop B-ALL. In one study, targeted sequencing of children with newly diagnosed B-cell ALL twenty-seven Ikzf1 coding variants were found in in nearly 0.87% of the patients. Ikaros also has a role in co-localizing with pericentromeric heterochromatin in lymphocytes and interaction with components of histone deacetylase (HDAC) complexes, including Sin3A and Sin3B (Sin3 complex), the chromatin remodeling Mi-2b ATPase (NuRD complex), and HDAC-1 and HDAC2.

Upon exposure to SMCAF, downregulation of NF-κB was noted, on a dose-dependent basis, in all cell lines, except K562 (see FIG. 4). This downregulation was most notable in RPMI-1788, and with smaller doses of SMCAF, where elimination of NF-κB was noted with 0.2 mg/ml, (p=0.020). In the Pre-B and B-cell cell lines, while the levels of this transcription factor linearly declined with doses of 0.4 mg/ml and 0.3 mg/ml of SMCAF (p=0.062 and p=0.001, respectively), with highest doses utilized, it was not completely eliminated. Of interest is that in the K562, a CML cell line, there was no statistically significant decline in the levels of NF-κB p65, even with highest dose of SMCAF i.e., 0.4 mg/ml used. (see FIG. 4) Changes noted in NF-κB are of interest. Constitutive activation of NF-κB complexes is found in the majority (39/42) of ALL patients without subtype restriction. These complexes are composed of p50-p50 and p65-p50 dimers. Prior reports indicate that proteasome inhibition in primary cultures of ALL cells results in a hyperphosphorylated form of IκBα and activation of upstream kinases. The latter triggers Iκ-Bα degradation and ultimately results in nuclear translocation of NF-κB. To observe these phenomenon, inhibitor of cellular proteolytic activities, including degradation of p65 needs to be suppressed with α-1 antitrypsin.

A number of studies indicate that NF-κB and associated regulatory factors are involved in cell proliferation and control of apoptosis in leukemia. In the T-cell ALL, it has been shown that Hes1, a canonical NOTCH target and transcriptional repressor, is responsible for sustaining IKK activation. Hes1 exerts its effects by suppression of the deubiquitinase CYLD, a negative IKK complex regulator. Expression of CYLD was reported to be significantly suppressed in T-cell ALL. NOTCH3 appears to be a link between signals leading to NF-κB activation and T-Cell tumorigenesis. A number of investigations have shown that activation of NF-κB prevents tumor necrosis factor induced cell death. TNF-related apoptosis-inducing ligands (TRAILs) and CD 95 have similar effects. In one study, inhibition of NF-κB by N-acetyl-L-leucinyl-L-leucinyl-L-norleucinal or transient overexpression of mutant IκBα was reported to result in a significant increase in induction of apoptosis by doxorubicin, an agent frequently used in treatment of leukemia. This was evident in both malignant lymphoid cell lines and leukemia cells resistant to this agent. Antagonization of NF-κB activity restored apoptotic sensitivity.

Given the role of NF-κB pathway in leukemia, inhibition of its activity by agents capable of blocking its pathway are of importance for investigation. NF-κB inhibitory molecules may potentially be used singularly or in combination with chemotherapeutic agents for the treatment of hematological malignancies. The finding of the downregulation of NF-κB, PAX-5 and Ikaros 55 and 75 kD under influence of SMCAF is of significance. The fact that SMCAF can change various transcription factors is novel and significant. This along with prior findings revealing that in patients with B-cell ALL, unlike controls, there are antibodies to SMCAF and exposure to these products in patients in full remission and long-term survivors results in re-development of characteristic genetics and cell surface phenotypes of the disease is of importance.

Microorganisms have been implicated in the etiology of malignant disorders, mainly due to their various effects resulting in genetic or epigenetic changes. It has been estimated that infectious microorganisms cause 18% of all malignant disorders. This is more pronounced in the developing countries where 26% of cancers are attributed to infections compared to 8% in the developed nations (8%). Some viruses are known to have the ability to alter the genetics of their host as a part of their cytopathogenesis. Incorporation of viral genome into the host chromosome can be incidental or as a part of the life cycle of these organisms. Viral genome integration can potentially lead to major cellular consequences including, gene disruption, insertional mutagenesis, oncogenesis and apoptosis. Mycoviruses are known to be able to alter their fungal host's phenotype, including pigmentation, morphology, sexual and asexual sporulation, production of aflatoxin, and growth. Some dsRNA mycovirus-containing fungal agents have been shown to alter the expression of genes involved in ribosomal synthesis and programmed cell death of the fungal host. If these organisms can exert any changes in humans or animals infected with mycovirus-containing fungi has not as yet been significantly explored. Mycoviruses dsRNA genomes or replication intermediates are detected by Toll-like receptor 3 (TLR-3) and can provoke interferon production in a TLR-3 dependent or independent fashion.

In the past, carcinogenic effects of fungi have been generally attributed to their mycotoxin production, and in case of *Aspergillus* species, to the aflatoxin. *Aspergillus* infected with a mycovirus, as is the case in that used in the above studies, does not produce any aflatoxin. This is attributed to the mycovirus infection, the removal of which results in the reproduction of aflatoxin. Indeed, this phenomenon is used as an advantage to advantage to control aflatoxin in grain crops. Therefore, the effects noted in up and downregulation of the transcription factors in the described experiments cannot be attributed to aflatoxin.

Rare reports of mycovirus-containing fungi affecting humans as a pathogen and their effects on the infected individual are available. An example is *Malassezia* species which produces various skin diseases including dandruff, seborrheic dermatitis, and atopic dermatitis. In one study, this organism was found to contain MrV40 mycovirus, which belongs to the Totiviridae family.

Prior published attempts to alter transcription factor activity, for therapeutic purposes, have been made in several types of cancer by direct mechanisms such as amplification or deletion of genes, point mutations, chromosome translocations, and alteration of expression, or indirectly via non-coding DNA mutations which can alter binding of the transcription factor. Means to alter the mode or levels of transcription factors for therapeutic purposes have also been made. This has included blockage of transcription factor-cofactor protein-protein interactions, prevention of transcription factor-DNA binding and modulating the levels of transcription factor. The latter has been attempted by altering levels of ubiquitylation and ensuing proteasome degradation or by inhibiting regulators of transcription factor expression. Other efforts to change the transcription factors have included targeting small molecule-based heterobifunctional Proteolysis Targeting Chimera (PROTACs) which modulates protein target levels by taking over the ubiquitin-proteasome system to bring about degradation of the target. Several new approaches targeting transcription factors have recently emerged. These include modulation of auto-inhibition, use of cysteine reactive inhibitors, targeting intrinsically disordered regions of transcription factors and combinations of transcription factor inhibitors with kinase inhibitors to block the development of resistance.

A relation of mycovirus-containing filamentous fungi and leukemogenesis is possible in light of the findings described herein, with the therapeutic approach being similar to that described herein.

Findings of the inventor indicate that patients with ALL have antibodies to a certain mycovirus-containing *Aspergillus flavus*. Furthermore, the studies revealed conversion of the mononuclear cells from ALL patients in full remission to the characteristic cell surface phenotypes and genetic markers characteristic of ALL upon exposure to the SMCAF. In light of the above findings, changes in the transcription factors under the influence of the SMCAF described in the above study are of significance. Finding that SMCAF can alter the expression of transcription factors in various cell lines is of significance and allows for preventive actions such as the production of antibodies specific to a mycovirus-containing *aspergillus* species or through a delivery vehicle such as a vaccine, blocking the development of acute lymphoblastic leukemia (ALL).

It is, therefore, apparent that there has been provided, in accordance with the various objects of the present invention, a method for detection of susceptibility to leukemia and lymphoma.

While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of this specification, claims and drawings appended herein.

What is claimed is:

1. A method for modifying transcription factors, the method comprising the steps of:
   obtaining cells from a normal individual or a leukemia patient; and
   exposing the cells to a product of a culture of a mycovirus-containing *Aspergillus flavus* to cause a modification to transcription factors;
   wherein the mycovirus is selected from the group consisting of Endornaviridae, Chrysoviridae, Megabirnaviridae, Quadriviridae, Partitiviridae, Reoviridae, and Totiviridae families.

2. The method for modifying transcription factors as defined in claim 1, wherein transcription factors are selected from the group consisting of NF-kB, PAX-5, IKAROS 55 kD and 75 kD transcription factors.

3. The method for modifying transcription factors as defined in claim 1, further comprising the step of measuring levels of the modified transcription factors.

4. The method for modifying transcription factors as defined in claim 3, further comprising the step of comparing the measured levels of the modified transcription factors to known levels and pre-exposure levels of transcription factors.

5. The method for modifying transcription factors as defined in claim 1, wherein the product of a culture of a mycovirus-containing *Aspergillus flavus* is a supernatant of the culture of a mycovirus-containing *Aspergillus flavus*.

6. The method for modifying transcription factors as defined in claim 1, wherein the modification of transcription factors is for therapeutic purposes.

7. A method for modifying transcription factors, the method comprising the steps of:

obtaining cells from a human or an animal; and exposing the cells to a product of a culture of a mycovirus-containing *Aspergillus flavus* to cause a modification to transcription factors;

wherein the mycovirus is selected from the group consisting of Endornaviridae, Chrysoviridae, Megabirnaviridae, Quadriviridae, Partitiviridae, Reoviridae, and Totiviridae families.

* * * * *